United States Patent [19]
Vaslow

[11] Patent Number: 4,753,641
[45] Date of Patent: Jun. 28, 1988

[54] EMERGENCY MEDICAL NEEDLE

[76] Inventor: Dale F. Vaslow, 1601 Sunset Dr., La Crosse, Wis. 54601

[21] Appl. No.: 95,121

[22] Filed: Sep. 10, 1987

[51] Int. Cl.⁴ .................................. A61M 5/32
[52] U.S. Cl. ........................................ 604/274
[58] Field of Search ............ 604/272, 273, 274, 411

[56] References Cited
U.S. PATENT DOCUMENTS

| | | | |
|---|---|---|---|
| 2,904,045 | 9/1959 | Owings | 604/274 |
| 3,119,391 | 1/1964 | Harrison | 604/274 |
| 3,906,932 | 9/1975 | Ayres | 604/274 X |
| 4,585,446 | 4/1986 | Kempf | 604/274 |

*Primary Examiner*—John D. Yasko

[57] ABSTRACT

An emergency medical needle for rapid cannulation of blood vessels that comprises a cannula with orifice(s) that face towards the vessel during insertion (so-called reverse cannula position) that enhances early return of blood to indicate penetration, a tip with cutting edges that biases the direction of insertion towards the vessel, and an extension of the bottom of the cannula that prevents penetration of the opposite wall, prevents coring, and prevents plugging so as to provide an early indication of penetration.

4 Claims, 1 Drawing Sheet

EMERGENCY MEDICAL NEEDLE

This invention relates to improvements in tubular needles for medical use in the cannulation of veins and arteries.

In emergency medicine there is a need for rapid access to the venous and arterial circulation for the purposes of administering drugs and fluids, obtaining specimens of blood for laboratory determinations, removing of blood in case of fluid overload, monitoring physiological parameters of circulation, and inserting catheters into the central circulation for physiological monitoring and cardiac pacing. In practice such access is attained with the use of cannulas. There are essentially three types of cannulas: (1) hollow needles, (2) indwelling plastic catheters inserted over a hollow needle, and (3) indwelling plastic catheters inserted either through a hollow needle or over a guide wire which is previously introduced through a needle. In each type of cannula initial access to the vessel is due to penetration of the vessel wall by the hollow needle tip. Further penetration introduces additional length of the needle and the associated catheter into the vessel lumen. It is important that there be some indication of the moment of insertion of the needle into the vessel lumen. Such indications include the resistance to motion that the experienced operator feels when the vessel wall is penetrated, and the appearance of blood at the proximal end (opposite the tip) of the needle. It is also important that the needle not penetrate the opposite wall of the vessel, a circumstance which leads to a hematoma and loss of the immediate use of that vessel for access to the circulation.

In the emergency medical situation it is often important to gain rapid access to the circulation in order to render life saving remedies. Such rapid access may be hindered by collapse or partial collapse of the peripheral circulation. Access to the collapsed vein is generally via the broad or flattened side which usually is nearly parallel to the skin surface. As the needle penetrates through the near wall, the close proximity of the opposite wall enhances the probability that it too will be penetrated and render the insertion attempt ineffectual. It is advantageous to gain access to the peripheral circulation because it minimizes simultaneous interference with centrally located procedures such as chest compression and ventilation. Although circulatory collapse is generally less of a problem in the centrally located veins, the complications are more dangerous. In particular, needle penetration of the opposite wall of a neck vein may result in a hematoma that can compromise the ventilation.

In the design of a needle for emergency access to the circulation the following design goals are considered:

It is the object of the present invention to provide a hollow needle which minimizes penetration of the opposite wall of the vessel.

It is the object of the present invention to provide a hollow needle that has its orifice close to the needle tip in order to give an early indication of vessel penetration as evidenced by the presence of blood at the proximal end of the needle resulting from backward flow of blood in the needle.

It is the object of of the present invention to provide a hollow needle with a cutting edge that directs the needle tip towards the vessel wall at an angle from the axis of the needle.

It is the object of the present invention to provide a hollow needle that minimizes coring and tearing, and thus minimizes danger and discomfort to the patient.

It is the object of this invention to provide a hollow needle that minimizes plugging in order to give an early indication of vessel penetration as evidenced by the presence of blood at the proximal end of the needle resulting from backward flow of blood in the needle.

It is the object of the present invention to provide a hollow needle that has its orifice(s) disposed to the bottom (so-called reverse cannula position) and sides in order to enhance the flow of blood or other fluids in collapsed vessels.

There is a considerable amount of prior art on needles and cannulas. However, each of the inventions comprising the prior art addresses some, but not all, of the objects of the present invention. The mose commonly used commercial hollow needle has the lancet shape with its double side bevels (also, see U.S. Pat. No. 2,697,438). The heel bevel lies in a plane at a small acute angle A to the right circular cylinder axis. The angle A ranges from about 10 to 20 degrees. The nose bevels lie in two planes that intersect on a line that lies in a plane that contains the cylinder axis and is perpendicular to the heel plane. This line passes through the point of the tip and forms an acute angle B with the cylinder axis where $B > A$ and $B < 90$ degrees. The purpose of this geometry is to reduce the coring effect. The cutting edges of the beveled surfaces bias the penetration of the needle towards the lumen of the vessel when the needle's orifice is oriented away from the vessel (normal cannula position). Its main disadvantage is that its point lies within its needle's outermost right cylindrical surface and therefore is the first portion of the needle tip to appose the opposite wall of the vessel upon entry into its lumen. Another needle with this disadvantage is that of U.S. Pat. No. 3,119,391 in which a center cross bar and cutting edge is employed to reduce coring. The lancet needle also sufferes from the problem of plugging in which the "core" is a a flap of vessel tissue oriented so as to fill the needle tip orifice and block its lumen, thus preventing an early indication of vessel penetration.

In a manner similar to the lancet needle, the needle in U.S. Pat. No. 4,490,139 has double side bevels except that the line forming the intersection of the nose bevel planes lies at an obtuse angle to the cylinder axis, i.e., $B > 90$ degrees and $B < 180$ degrees. Therefore, the point of the tip of this needle lies on the inside right cylindrical surface. Thus, in comparison to the lancet needle the point of the tip is displaced away from the outer right cylindrical surface towards the side of the orifice by a small distance equal to the thickness of the needle wall. Therefore this needle retains the main disadvantage of the lancet needle to a large extent.

In the Huber needle, U.S. Pat. Nos. 2,717,599 and 2,717,600, the Sorensen needle, U.S. Pat. No. 2,746,454, the modified Huber needle, U.S. Pat. No. 3,924,617, and the coneshaped tip needles, U.S. Pat. Nos. 2,416,391 and 4,565,545, the point of the tip is displaced towards the side of the orifice. This feature reduces the probability of penetrating the opposite wall of a vessel. All of these needles, however, are used in the normal cannula position, and therefore retain the disadvantages of that type of needle. These disadvantages have been discussed in U.S. Pat. No. 4,368,738.

The reverse cannula position needle, U.S. Pat. No. 4,368,738, has two cutting edges formed from ground surfaces that lie in two planes that meet at an obtuse angle. The cutting edge of the nose tip forms an obtuse angle with the cylinder axis, while the cutting edge of the heel forms a small acute angle with the cylinder axis. When the needle penetrates the vessel wall it follows a curve in the shape of the cutting edges; the nose edge biases the penetration of the needle towards the vessel wall, while the heel edge biases the penetration away from the opposite vessel wall. The effect is to minimize the interaction of the tip point with the opposite wall, particularly in a vessel whose lumen is open to a diameter larger than the dimension of the nose. In a collapsed or partially collapsed vessel, however, the tip point may appose the opposite wall and damage or penetrate its surface. Furthermore, in the collapsed vessel the orifice of the needle is "covered" by the vessel wall, and requires rotation of the needle by 90 degrees to keep the cannula opening free.

The 4-sided equilateral needle in U.S. Pat. No. 3,633,580 has two orifices, both of which may be oriented sideways during needle penetration. The advantage of sideways orientation of the orifices occurs in a collapsed vessel. In a collapsed vessel the needle acts as a spacer, opening a channel on either side of the needle, while the top and the bottom of the needle are covered by the vessel wall. The 4-sided equilateral needle has disadvantages. The four substantially equilateral cutting edges eliminate the penetration bias required to aid in penetrating the vessel wall, and may lead to damage of the opposite vessel wall. Furthermore, the planar shape of the bottom surface of the needle does not provide optimal separation of the tip point from the opposite vessel wall.

SUMMARY OF THE INVENTION

Accordingly, the invention comprises a method and apparatus for cannulation of arteries and veins. The invention provides a means to acquire access to the lumen of an artery or vein via an induced opening in the wall of the same, detect the moment of insertion via backward flow of blood from the vessel, and prevent penetration of the opposite wall of the vessel which would render the access ineffectual.

The preferred embodiment of this invention is a hollow needle that may be used along or in conjunction with a catheter that is inserted over the hollow needle after initial access to the vessel lumen is attained.

This invention comprises a hollow needle having a pointed distal end with a closely approximated orifice(s) for the exchange of fluids across its aperture and which communicate with the lumen of the needle shaft. The lumen extends along the length of the needle to the orifice at the proximal end which communicates with free space or other attached devices such a syringe or connective tubing.

The pointed distal end and the closely approximated orifice(s) comprise the tip of this invention, and it is the particular design of this tip which renders the advantages of this invention over prior art. In the preferred embodiment of this invention the tip is geometrically symmetric to a plane that bisects the shaft of the needle at its midline, i.e., it has mirror symmetry. The tip has top and bottom sides that are distinguished by their orientation to the vessel during insertion. During insertion the bottom faces the vessel, in the so-called reverse cannula position.

The top surface of the needle tip, as viewed from the top, has a triangular shape that is bounded by two lateral cutting edges that meet at the point of the tip. In transverse cross section to the needle axis the top surface is either nearly planar or somewhat convex upwards in shape. The cutting edges slope towards the bottom side of the needle as they approach their intersection at the point. This feature provides the needle with a penetration bias that helps to direct the needle through the vessel wall into the vessel lumen.

The bottom side of the needle comprises the orifice(s) and a midline stucture, hereafter referred to as the jaw, that extends from the base of the tip towards the point. The orifice(s) are bounded by the cutting edges laterally and by the jaw medially. The jaw may bridge the gap from the base to the point, in which case there are two orifices, or it may partially bridge the gap, in which case the two halves of the single orifice are joined by an isthmus near the point and at the midline. The faces of the orifices form apertures that communicate with the needle lumen, and they generally face downward, forward and laterally. This disposition of the orifices is advantageous because they rapidly communicate with the vessel lumen upon penetration of the vessel wall by the needle tip, and optimally maintain communication with the lumen of a collapsed vessel.

The jaw is a midline structure on the bottom side of the needle that forms at the base of the needle and extends towards the point or nose, generally narrowing towards the point. The bottom surface of the jaw generally conforms with the forward projection of the needle shaft surface beginning at the base of the tip until it reaches a bend in the jaw, hereafter referred to as the chin. Beyond the chin the jaw surface departs from the projected surface of the shaft, reaching towards the point or towards the top structure recessed from the point. The advantage of the jaw with its protruding chin is that with correct insertion of this invention into a vessel the chin will act as an anti-snagging device by contacting the opposte vessel wall, instead of the point, and therefore preventing penetration of the opposite vessel wall by the point. A further advantage of the jaw is that helps to reduce coring. A second further advantage of the jaw is that it prevents the core from plugging the needle lumen and, therefore, the return of blood, which is used to indicate penetration of the needle into the vessel, is not blocked. The anti-plugging feature is due to two separate effects: the first is the direct interference of the jaw with the cored tissue to prevent it from entering the needle lumen; and the second somewhat less obvious effect is the formation of the tissue flap (comprising the core) on the top side of the needle tip, away from the orifice(s), and thus in a position where it is less likely to enter and block the needle lumen. The latter effect is due to the force that the jaw exerts on the tip towards the top of the needle tip, thus causing the cutting edges to cut the flap of vessel wall tissue on the opposite side to the orifice(s). Various other features of the method and apparatus of the present invention will become obvious to those skilled in the art upon reading the disclosure set forth hereinafter.

DETAILED DESCRIPTION OF THE PREFERRED EMBODIMENT

Figure 1:
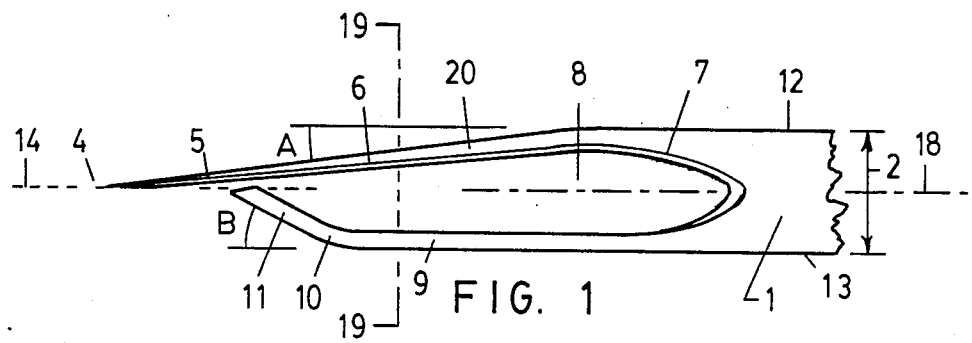
FIG. 1 is a side view of a needle tip constructed in accordance with the invention.
Figure 2:
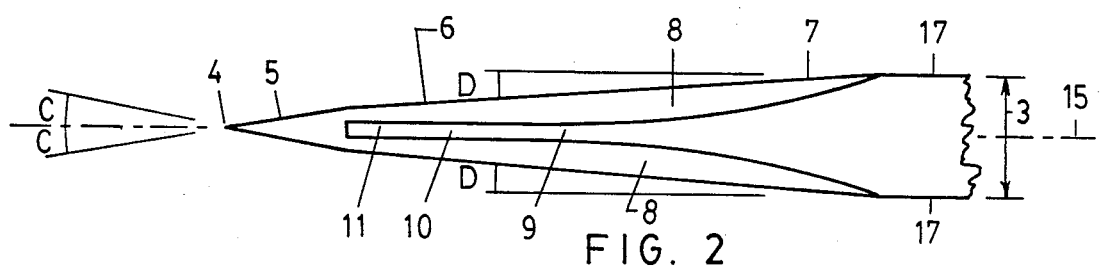
FIG. 2 is a bottom view of the needle shown in FIG. 1.
Figure 3:
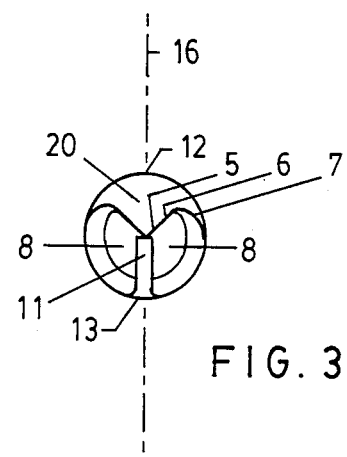
FIG. 3 is a front view of the needle shown in FIG. 1.

FIGS. 1, 2, and 3 illustrate the side, bottom, and front views of a surgical needle tip constructed in accordance with the invention. The body or shaft 1 of the hollow needle extends backwards to its proximal end (not shown) where it is fastened to a suitable holder or flange and where the needle lumen communicates with free space or some other device such as a syringe. The body 1 extends forward to the distal end which comprises the tip, mainly featured in FIGS. 1, 2, and 3. As shown, the body has a cylindrical shape, but other tubular shapes are intended as well. The vertical height of the body 2 is shown in FIG. 1, and the horizontal width 3 is shown in FIG. 2.

The tip has substantially geometric mirror symmetry to a plane containing the midline 15 and the vertical line 16. The tip has a top 12 and a bottom 13. During penetration of a vessel the bottom is oriented towards the vessel. The point 4 is the most distal portion of the tip, and is usually the first part of the needle to contact the vessel during penetration. The point 4 lies on the point longitudinal axis 14, which is parallel to, but does not necessarily coincide with, the needle axis 18 which is generally central to the tubular needle.

The top member of the tip 20 has a triangular-like shape in its horizontal projection and is bounded by the base of the tip and the cutting edges 7, 6, and 5, where edge 6 is a continuation of edge 7, and edge 5 is a continuation of edge 6, and where the two edges 5 meet at the point 4. In transverse cross-section at 19—19 the top member 20 appears either planar or convex upwards in shape, though flattened in comparison to the tranverse curvature of the body 1 at the top 12. In the horizontal plane the tangential projection of the edge 5 makes an acute angle C with the needle axis and similarly edge 6 makes an acute angle D with the needle axis where the magnitude of angle C is greater than or equal to the magnitude of angle D. The edge 7 continues backwards from the edge 6, curving towards the widest portion of the needle body 17 where it terminates thereabouts.

In the side view, FIG. 1, it is shown that the top member 20 slopes towards the bottom side, i.e., vertically downwards, from the base of the tip to its point. The line tangent to the top member edge 5 at the point 4 makes a small acute angle A with the point longitudinal axis. Edges 5 and 6 provide the tip with a penetration bias that directs the tip at an angle to its axis towards the vessel as the penetration is initiated. Edge 7, on the other hand, provides the tip with a penetration bias that directs the lateral motion of the tip opposite to that of edges 5 and 6, particularly near its basal portion. This aids in the prevention of the penetration of the opposite wall of the vessel.

The bottom member 9, 10, and 11 has a triangular-like shape in horizontal projection with its base location at the basal portion of the tip and its narrow part towards the point. It is the intention of this invention that the bottom member, hereafter referred to as the jaw, may vary considerably in its preferred embodiments. The jaw is comprised of three portions, a neck 9, a chin 10, and a bridge 11. The neck 9 adjoins the basal part of the tip and is an extention of the needle body in a general forward axial direction, becoming generally more narrow towards the point. The bridge 11 is a short continuation of the neck that bends upwards from the chin towards the top member 20 either at a location near the point 4 or a location backwards from the point. A tangential line to the bridge in the plane of symmetry forms an acute angle B with the point longitudinal axis. In general the magnitude of the angle B is greater than the magnitude of the angle A. The bridge 11 may abut against the top member as shown in the preferred embodiment in FIGS. 1, 2, and 3, or it may terminate short of the top member 20 leaving a gap between the bridge 11 and the top member 20. In the preferred embodiment shown in FIGS. 1, 2, and 3 all of the components of the jaw have non-cutting edges. In another preferred embodiment the distal portion of the bridge has a short cutting edge. The jaw with its protruding chin acts as an anti-snagging device to prevent penetration of the vessel opposite wall after penetration of the vessel's near wall is initiated. During the penetration of the vessel's near wall the jaw, in particular its chin, contacts the vessel's near wall and exerts a force away from the vessel's opposite wall, thus inhibiting possible penetration of the opposite wall by the needle point. A similar action may ensue once the chin has entered the vessel's lumen and contacted the vessel's opposite wall. Furthermore, the jaw acts like a spacer to prevent point contact with the vessel's opposite wall. A further action of the jaw is to prevent coring and plugging.

The relative disposition of the top member 20 and the jaw 9, 10, and 11 is to establish two orifices, each of which faces laterally, downward, and forward. In the preferred embodiment in FIGS. 1, 2, and 3 the two orifices are separate and distinct. In another preferred embodiment in which there is a gap between the bridge and the top member 20, the two halves of a single orifice are joined by an isthmus at the gap. The faces of the orifices form apertures that communicate the vessel lumen advantageously to the sides of the needle.

The invention claimed is:

1. A medical needle comprising a cannula (i.e., a hollow body) of generally cylindrical shape having two ends, such ends consisting of an integral pointed distal end and a proximal end, each of such ends having one or more orifices that communicate with the lumen of said body; said distal end having cutting edges that meet at the tip, said cutting edges lie within a flat, smooth, or piecewise smooth curved plane whose tangent planes of the distal edges intersect proximally with the top of the cannula body or its distal projected surface, and whose tangent planes of the proximal edges intersect distally with the top of the cannula body or its distal projected surface; said orifice(s) having lateral and medial edges, said lateral edges lie in a curved plane that intersects, approximates, or coincides with the plane of the cutting edges at the tip and approximates, coincides with, or diverges away from the plane of the cutting edges proximally such that its proximal tangent planes intersect proximally with the bottom of the cannula, said lateral orifice edges meet the medial orifice edges at or near the widest portion of the cannula body, and said medial orifice edges form the lateral edges of an extension of the bottom of the cannula that generally narrows in width distally and extends a distance not beyond the tip; and said extension of the bottom of the cannula serves to prevent penetration of the tip into the opposite wall of the penetrated vessel, prevent plugging of the needle lumen and thus enhance the early return of blood to the proximal end of the cannula where it provides an indication of penetration into the vessel lumen, and prevents coring of the vessel tissue.

2. A cannula as claimed in claim 1, wherein the distal extension of the bottom of the cannula projects upwards towards the tip to partially block the distal lumen.

3. A cannula as claimed in claim 1 and 2, wherein the distal extension of the lower portion of the cannula body makes contact with the tip.

4. A cannula as claimed in claim 1 and 2, wherein the distal extension of the lower portion of the cannula body is contiguous with the central partition of a bipartite lumen.

* * * * *